United States Patent [19]

Jefson et al.

[11] Patent Number: 4,847,245

[45] Date of Patent: Jul. 11, 1989

[54] N-DEMETHYLEFROTOMYCIN

[75] Inventors: Martin R. Jefson, Stonington, Conn.; Jeiji Kaneda, Aichi, Japan; Satoshi Nishiyama, Aichi, Japan; Junsukse Tone, Aichi, Japan

[73] Assignee: Pfizer Inc., New York, N.Y.

[21] Appl. No.: 182,553

[22] Filed: Apr. 18, 1988

[51] Int. Cl.$^4$ .................. C07G 3/00; C07G 11/00; C12P 19/58; C12N 1/20

[52] U.S. Cl. ......................... 514/54; 536/4.1; 536/16.8; 435/253.2; 435/77

[58] Field of Search ............... 536/4.1, 16.8; 514/54.0

[56] References Cited

U.S. PATENT DOCUMENTS

| | | | |
|---|---|---|---|
| 4,024,251 | 5/1977 | Maiese et al. | 424/181 |
| 4,065,356 | 12/1977 | Maiese et al. | 435/886 |
| 4,262,002 | 4/1981 | Dewey et al. | 435/118 |
| 4,264,607 | 4/1981 | Dewey et al. | 435/118 |
| 4,482,545 | 11/1984 | Bochis et al. | 536/16.8 |

OTHER PUBLICATIONS

Monographs 887 and 6083, Merck Index, 10th Ed, Merck and Co., Rahway, N.J., 1983, pp. 127 and 891.

*Primary Examiner*—Johnnie R. Brown
*Assistant Examiner*—Pamela S. Webber
*Attorney, Agent, or Firm*—Peter C. Richardson; J. Trevor Lumb; Robert K. Blackwood

[57] ABSTRACT

N-Demethylefrotomycin, a valuable new antibiotic substance, is produced by the microbial conversion of mocimycin using a novel, efrotomycin-producing, microbial species ATCC 53758.

2 Claims, No Drawings

N-DEMETHYLEFROTOMYCIN

BACKGROUND OF THE INVENTION

The present invention is directed to N-demethylefrotomycin, having the formula (I) below; and its preparation by means of microbial glycosylation of mocimycin, having the formula (II) below, using efrotomycin-producing microbial species ATCC 53758.

Efrotomycin, which possesses a methyl group on pyridone nitrogen, but is otherwise of the formula (I), is the subject of Maiese et al., U.S. Pat. No. 4,024,251. Mocimycin is the subject of monograph 6083, Merck Index, 10th Edition, Merck & Co., Rahway, N.J., 1983, p. 891. The corresponding pyridone-N-methylated compound otherwise corresponding to mocimycin is known as aurodox; see monograph 887, loc. cit., p. 127.

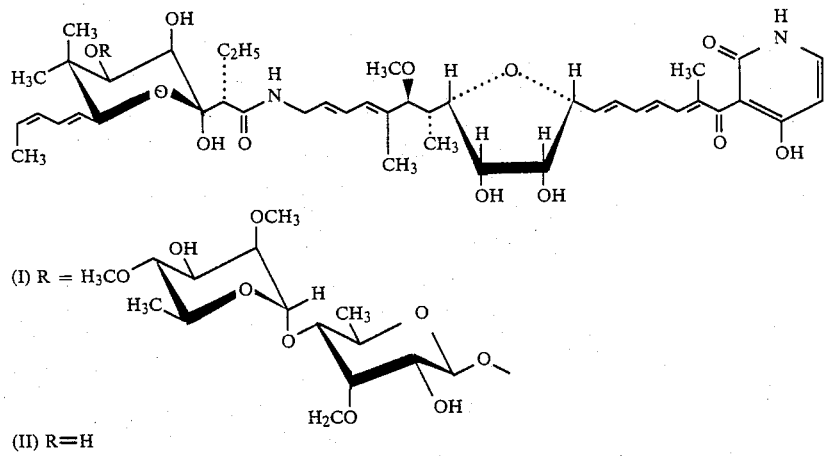

(I) R = H$_3$CO- [sugar group shown]

(II) R=H

SUMMARY OF THE INVENTION

The present invention is directed to N-demethylefrotomycin (I) and its preparation by the fermentation of an efrotomycin producing culture of ATCC 53758 in the presence of mocimycin (II) as precursor.

N-Demethylefrotomycin possesses antibacterial utility typical of the kirromycin group of antibiotics, which includes efrotomycin itself, as detailed in Maisse et al., cited above.

DETAILED DESCRIPTION OF THE INVENTION

The culture capable of producing present N-demethylefrotomycin (I) by fermentation of mocimycin (II) is designated Nocardia sp., and has been deposited under the Budapest Treaty in The American Type Culture Collection, Rockville, Md. as the type culture under their accession number ATCC 53758. Permanency of the deposit of this culture at The American Type Culture Collection at Rockville, Md. and ready accessibility thereto by the public are afforded throughout the effective life of the patent in the event the patent is granted. Access to the culture is available during pendency of the application under 37 CFR 1.14 and 35 USC 122. All restrictions on the availability to the public of the culture deposited will be irrevocably removed upon granting of the patent.

This novel culture was derived from a soil sample, and is identified in the culture collection of Pfizer Inc. as N747-44. Operation of the present invention does not require a detailed taxonomical description of this culture, only the availability of the culture, and methods using same for the preparation of N-demethylefrotomycin which are detailed below. Nevertheless, applicant here provides by amendment the results of toxonomical studies by Dr. L. H. Huang which were underway at the time the present application was filed.

This culture was found to produce the narrow substrate hyphae and the aerial mycelium which fragments into rods of varying length at maturity.

A slant culture of the microorganism was planted into ATCC 172 broth and grown for four days at 28° C. on a shaker. It was then centrifuged for 20 minutes, washed three times with sterile distilled water, and planted on media commonly used for identification of members of the Actinomycetales.

The cultures were incubated at 28° C. and the results read at varying times, but most commonly at fourteen days. The colors were described in common terminology, but exact colors were determined by comparisons with color chips from *The Color Harmony Manual*, fourth edition. The methods of whole-cell amino acid and sugar analyses are those described in Becker et al., Appl. Microbiol., vol. 12, pp. 421–423 (1964), and in Staneck et al., Appl. Microbiol., vol. 28, pp. 226–231 (1974) and Lechevalier, J. Lab. Clin. Med., vol. 71, pp. 934–944 (1968), respectively.

The culture was identified as follows:

Yeast Extract-Malt Extract Agar (ISP #2 medium, Difco) - Growth good, white to pale pink (4 ca) raised, wrinkled; aerial mycelium white; reverse yellowish orange (3 ia); no soluble pigment.

Oatmeal Agar (ISP #3 medium, Difco) - Growth good, white, raised, smooth; aerial mycelium white; pale yellowish orange (3 ea); soluble pigment cream (2 ca).

Inorganic Salts-Starch Agar (ISP #4 medium, Difco) - Growth good, pale pink to pink (3 ca, 4 ca), raised smooth to slightly granular; aerial mycelium pale pink (3 ca, 4 ca); reverse pale yellowish orange (3 ea, 3ga); no soluble pigment.

Glycerol-Asparagine Agar (ISP #5 medium, Difco) - Growth moderate, pale pink cream (3 ca, 4 ca), slightly raised, smooth to granular; aerial mycelium same as surface; reverse pale yellowish orange (3 ea, 3 ga); no soluble pigment.

Czapek-Sucrose Agar (Waksman, "The Actinomycetes", vol. 2, medium #1, p. 328, 1961) - Growth good, pale pink (4 ca), raised, smooth, aerial mycelium pale pink (4 ca); reverse pale pink (3 ca); no soluble pigment.

Glucose-Asparagine Agar (ibid., medium #2) - Growth good; white to yellowish orange (3 ea, 3 ia), moderately raised, smooth to granular but may be wrinkled near edge; aerial mycelium white; reverse yellowish orange (3 ea, 3 ga); no soluble pigment.

Gordon and Smith's Tyrosine Agar (Gordon and Smith, J. Bacteriol., 69:147-150, 1955) - Growth moderate, cream to yellowish (2 ca, 2 ic); moderately raised, smooth to wrinkled; aerial mycelium white; reverse yellowish (2 ga, 2 lc); soluble pigment yellowish (2 ga).

Calcium Malate Agar (Waksman, Bacteriol. Rev. 21, 1-29 1957) - Growth moderate to good, white to pale pink (near gray series 5 ba), moderately raised, smooth to slightly granular; aerial mycelium white to pale pink (near gray series 5 ba); reverse cream to pale pink (2 ca, 3 ca); no soluble pigment.

Casein Agar (Gordon and Smith, ibid.) - Growth good, white, pale gray to orange (near gray series 3 cb, 4 la); moderately raised, smooth to wrinkled; aerial mycelium white to pale gray (near gray series 3 cb); reverse yellowish orange (3 la); with orange (4 ia) soluble pigment.

Bennett's Agar (Waksman, loc. cit., medium #30, p. 331) - Growth excellent, white to pale pink (4 ca), raised, wrinkled, aerial mycelium same as surface; reverse yellowish orange (3 ga, 3 ia); soluble pigment none to pale yellowish (2 ea).

Emerson's Agar (ibid., medium #28, p. 331) - Growth good, pale gray, yellowish to yellowish orange (near gray series 3 cb, 2 ga, 3 ga); raised, wrinkled; aerial mycelium pale gray (near gray series 3 cb); reverse yellowish (2 lc); soluble pigment yellowish brown (3 lc).

Nutrient Agar (ibid., medium #14, p. 330) - Growth moderate, pale yellowish orange (near 3 ea), cream (2 ca), slightly raised, smooth to wrinkled; aerial mycelium sparse, white; reverse same as surface; no soluble pigment.

Gelatin Agar (Gordon and Mihm, J. Bacteriol. 73, 15-27, 1957) - Growth moderate to good, pale yellowish, yellowish orange to yellowish brown (2 ea, 3 ga, 3 gc), moderately raised, smooth, no aerial mycelium; reverse same as surface; soluble pigment pale yellowish (2 ea).

Starch Agar (ibid.) - Growth moderate to good, white to pale yellowish orange (3 ia), moderately raised, smooth but wrinkled toward edge; aerial mycelium sparse, white; reverse same as surface; no soluble pigment.

Potato Carrot Agar (Lechevalier, Lab. Clin. Med., 71, 934-944, 1968, but use only 30 g. potatoes, 2.5 g. carrots and 20 g. agar) - Growth moderate to good, white to pale yellowish orange (near 3 ca), moderately raised, smooth; aerial mycelium same as surface; reverse pale yellowish orange (3 ea); no soluble pigment.

Tap Water Agar (2%) - Growth moderate, white, moderately raised, smooth; aerial mycelium white; reverse colorless to cream (2 ca); no soluble pigment.

Gauze's Mineral Medium 1 (Gauze et al., Problems in the Classification of Antagonistic Actinomycetes, English Ed., p. 13, 1957) - Growth good, white to pale pink (4 ca), raised, smooth to slightly wrinkled; aerial mycelium same as surface; reverse cream to yellowish orange (2 ca, 3 ga); soluble pigment pale yellowish (2 ea).

Gauze's Organic Medium 2 (ibid.) - Growth good, tan to yellowish orange (3 gc, 3 ga), moderately raised, wrinkled; aerial mycelium sparse, white; reverse yellowish (2 ga, 2 lc); soluble pigment yellowish brown (3 lc).

Morphological Properties - The morphological properties were observed after two weeks of incubation on inorganic salts-starch agar: the substrate hyphae branched, straight or curved or wavy, 0.5-0.9 micron diam.; the aerial hyphae pale pink in mass, fragmenting into rods of varying lengths, 1.2-3.0×0.6-1.0 micron or longer than 3.0 micron; hyphal fragments smooth, as revealed by scanning electron microscopy.

Biochemical Properties - Melanin not produced; hydrogen sulfide produced; gelatin liquefied; starch not hydrolyzed; nitrate not reduced to nitrite; excellent growth but no disintegration on either Jensen's or Levine and Schoenlein's cellulose broth; clearing but no coagulation on milk; casein digestion positive; tyrosine digestion positive; calcium malate digestion negative. Carbohydrate utilization: glucose, arabinose, fructose, mannitol, raffinose, rhamnose, sucrose, xylose, adonitol, cellobiose, galactose, glycerol, lactose, maltose, mannose, melibiose, alpha-methyl-D-glucoside, ribose, sorbitol, starch, and trehalose utilized; melezitose doubtfully utilized; dulcitol, erythritol, and sorbose not utilized. Acid production: acid produced from glucose, arabinose, fructose, inositol, mannitol, raffinose, rhamnose, sucrose, xylose, cellobiose, galactose, glycerol, lactose, maltose, mannose, melezitose, melibiose, alpha-methyl-D-glucoside, ribose, sorbitol, starch, and trehalose; acid not produced from adonitol, dulcitol, erythritol, salicin, and sorbose.

The other positive tests included utilization of acetate, citrate, lactate, oxalate, propionate, pyruvate and succinate; hydrolysis of esculin, hippurate and urea; and decomposition of xanthine, and hypoxanthine. The following tests were negative: utilization of benzoate, dextrin, malate, mucate, and phenol; decomposition of adenine and resistance to lysozyme.

Temperature Relations

| 21° C. | 28° C. | 37° C. | 45° C. |
| --- | --- | --- | --- |
| Poor to Moderate Growth | Good Growth | Moderate to Good Growth | No Growth |

Whole-Cell Analysis - The whole-cell hydrolysates contained meso-diaminopimelic acid, galactose, and arabinose.

The culture N747-44 is characterized by the white, pale pink to yellowish orange colonies; the yellowish, pale yellowish orange to yellowish orange substrate mycelium; and the white to pale pink aerial mycelium which may fragment into sections of varying lengths. All of the sugars except for melezitose, dulcitol, erythritol, salicin, and sorbose were utilized. Acid was produced from all of the sugars except for adonitol, dulcitol, erythritol, salicin, and sorbose. Xanthine and hypoxanthine but not adenine were decomposed. Esculin, hippurate, and urea were hydrolyzed. The cell wall, which contained meso-diaminopimelic acid, galactose, and arabinose, is of the type IV, as defined by Lechevalier and Lechevalier. On the basis of the data mentioned above, the culture N747-44 is considered as a member of the genus Norcardia and designated Norcardia sp.

Present N-demethylefrotomycin (I) is readily produced by fermenting the microbial species ATCC 53758 in the presence of mocimycin (II).

In the usual manner of carrying out the fermentation, an inoculum is first prepared by scraping vegetative cells, growing on a suitable media, from slants or Roux bottles which have been inoculated with the microbial sp. ATCC 53758. The resulting vegetative cells are in turn used to inoculate shake flasks or inoculum tanks in which fermentation proceeds to completion in about 4-8 days at from about 24° to about 36° C. under submerged conditions, with agitation and aeration, on media consisting of carbohydrate sources such as sugars, starches, glycerol; organic nitrogen substances such as soybean meal, casamino acids, yeast extract; growth substances such as grain solubles, fish meal, cotton seed meal; mineral salts containing trace elements such as iron, cobalt, copper, zinc, etc. and calcium carbonate or phosphates as buffering agents. Mocimycin is generally added portionwise over the 4-8 day period required to complete the fermentation, for example in a 7-day fermentation required to complete fermentation in a 500 mL shake flask, the mocimycin is added in 3 equal portions, at the end of day 4, day 5 and day 6.

After growth has been completed, the antibiotics are readily recovered by extracting the whole broth with an organic solvent such as n-butanol, methylisobutyl ketone, or chloroform at pH ranges from 4.0 to 8.0. Conveniently, the extracts are evaporated to dryness, and the residue subjected to chromatography on Sephadex LH20 to produce a clean mixture of N-demethylefrotomycin and efrotomycin (the latter being the usual product of the fermentation). This mixture is then separated by further chromatography, e.g., on silica gel, to produce purified N-demethylefrotomycin.

The antibacterial activity of the compound of the formula (I) is demonstrated by measuring its minimum inhibitory concentrations (MIC's) in mcg./ml. against a variety of microorganisms in brain heart infusion (BHI) broth. Generally twelve 2 fold dilutions of the test compound are employed, with initial concentration of the test drug being in the range of 50 to 200 mcg./ml. The susceptibility (MIC) of the test organism is accepted as the lowest concentration of compound capable of producing complete inhibition of growth as judged by the naked eye. Antibacterial activity typical of N-demethylefrotomycin (I) is shown in the Table I.

TABLE I

| In vitro Activity of N—Demethylefrotomycin | | | |
|---|---|---|---|
| | | Replicate MIC Values | |
| | | Day 1 | Day 2 |
| Staph. aureus | 006 | (a) | (a) |
| E. coli | 124 | (a) | (a) |
| Past. mult | 006 | 6.25 | — |
| | 013 | — | 12.5 |
| | 048 | 3.12 | 6.25 |
| Past. haem. | 010 | 3.12 | — |
| | 018 | 12.5 | 12.5 |
| | 046 | 25 | 12.5 |
| | 061 | 25 | 3.12 |
| Morax. bovis | 001 | 6.25 | 3.12 |
| Strep. zooedid. | 001 | (a) | — |
| Lact. acidoph. | 001 | 12.5 | — |
| Lact. sp. | 001 | (a) | — |
| Clost. perf. | 006 | 12.5 | — |
| | 009 | 12.5 | — |
| | 002 | 12.5 | — |
| Acto. pyog. | 002 | 12.5 | — |
| | 008 | 12.5 | — |
| | 011 | 100 | — |

TABLE I-continued

| In vitro Activity of N—Demethylefrotomycin | | | |
|---|---|---|---|
| | | Replicate MIC Values | |
| | | Day 1 | Day 2 |
| Hemoph. pleur. | 004 | 12.5 | — |
| | 005 | 12.5 | — |
| | 024 | (a) | — |
| Fusob. necro. | 004 | 25 | — |
| | 006 | 6.25 | — |
| Trepo. hyodis. | 001 | 1.56 | — |
| | 002 | 0.78 | — |
| | 007 | 1.56 | — |

(a) greater than 100.

Additionally, compound (I) is tested in vivo by the well-known mouse protection test, or by a microbiological (bioassay) determination of serum levels in a variety of mammals (e.g., mouse, rat, dog). For example, at subcutaneous doses of either 100 mg./kg. or 25 mg./kg., there was survival of 5/5 mice infected i.p. with multilethal amounts of Past. haem. 010.

N-Demethylefrotomycin is expected to find primary use in animals in the treatment of infections due to susceptible microorganisms. It is dosed at a level of 2.5-100 mg./kg. per day, preferably 5-50 mg./kg./day, in single or divided doses. Variation in dosage will be made depending upon the animal and upon the particular susceptibility of the microorganism. These compounds are dosed orally or parenterally, the preferred route being parenteral in large animal veterinary and veterinary office practice, and oral when animal pets are dosed at home. The susceptibility of microorganisms isolated in the field is routinely tested in bacteriology laboratories by the well-known disc-plate method. Compound (I) is generally the compound of choice when it shows a relatively large zone of inhibition against the bacteria causing the infection to be treated.

N-Demethylefrotomycin also finds use as an antibacterial, growth-promoting feed additive in farm animals. N-Demethylefrotomycin is also useful topically in the treatment of superficial infections in animals, including man.

Preparation of optimal dosage forms will be by methods well known in the pharmaceutical art. For oral administration, the compounds are formulated alone or in combination with pharmaceutical carriers such as inert solid diluents, aqueous solutions or various nontoxic organic solvents in such dosage forms as gelatin capsules, tablets, powders, lozenges, syrups and the like. Such carriers include water, ethanol, benzyl alcohol; glycerin, propylene glycol, vegetable oils, lactose, starches, talc, gelatins, gums and other well known carriers. The parenteral dosage forms required for the above systemic use are dissolved or suspended in a pharmaceutically-acceptable carrier such as water, saline, sesame oil and the like. Agents which improve the suspendability and dispersion qualities can also be added.

For the topical treatment of superficial infections in animals, including man, caused by susceptible microorganisms, the compound (I) is formulated by methods well known in the pharmacist's art into lotions, ointments, creams, salves, gels, or the like at concentrations in the range 5-200 mg./cc. of the dosage form, preferably in the range 10-100 mg./cc. The dosage form is applied at the site of infection ad libitum, generally at least once a day.

When used as an animal growth promotant, the medication can be added directly to a feed supplement or to the feed as such, or in the form of a premix or concentrate in a carrier. Suitable carriers are usually milled or powdered solids, such as various meals (for example, soybean oil meal, linseed oil meal, corncob meal) or mineral mixes such as are commonly employed in animal feeds. The premix is then further blended into additional carrier, or a small portion of feed, to produce a feed supplement. Alternatively the premix is blended with the entire ration of a nutrionally balanced feed. In such use, the level in food will generally be in the range of 2-100 ppm. When used in a feed supplement the level will be generally higher, for example 20-1000 ppm in a feed supplement which represents 10% of the total feed ration.

The present invention is illustrated by the following example. However, it should be understood that the invention is not limited to the specific details of this example.

EXAMPLE

Microbial culture ATCC 53758, initially grown on slants, was transferred to 10×500 mL shake flasks each containing 100 mL of the following fermentation medium: glucose 10 g., dextrin 5 g., corn steep liquor 5 g., blood meal 5 g., and CaCO$_3$ 3g., made up to 1 liter with tap water. The flasks were incubated and shaken for 7 days at 28° C. At the end of 4 days, 5 days and 6 days, 6 mg. of mocimycin (Pijnacker et al., U.S. Pat. Nos. 3,923,981 and 3,927,211) was added to 9 of the 10 flasks. The total mocimycin added was 9 x 3 x 6 mg. = 162 mg). The tenth shake flask, to which no mocimycin was added, was used as control fermentation. The production of efrotomycin and N-demethylefrotomycin, and the unconsumed mocimycin was monitored by HPLC on a 4.6 mm×15 cm packed with Chemcosorb 50DS-H using 0.5% acetic acid in 45% CH$_3$CN as eluant, a flow rate of 1 mL/minute and UV detection at 254 microns, resulting in the following assays:

| Time (days) | Antibiotic Levels (mcg/mL) | | | Control |
|---|---|---|---|---|
| | Fermentation of Mocimycin | | | |
| | Efroto-mycin | N—Demethyl-efrotomycin | Moci-mycin | Efroto-mycin |
| 5 | 200 | 50 | 0 | 150 |
| 6 | 250 | 150 | 20 | 250 |
| 7 | 300 | 200 | 70 | 330 |

No mocimycin or N-demethylefrotomycin was detected in the control flask.

At the end of seven days, the combined broth (900 mL) from the nine non-control flasks was extracted 2×1 liter of ethyl acetate. The organic layers were combined, evaporated in vacuo, the residue taken up in minimal methanol and column chromatographed on 400 mL Sephadex LH20 using methanol as eluant and collecting 20 mL fractions. Fractions 8-12 were combined and stripped to yield 396 mg. of a mixture of efrotomycin and N-demethylefrotomycin, which was chromatographed on seven 20×20 cm×0.25 mm silica gel plates using 75:25:1 CHCl$_3$:CH$_3$OH:conc. NH$_4$OH as eluant in a single pass. There was thereby recovered 140 mg. of efrotomycin (Rf 0.46) and 100 mg. of N-demethylefrotomycin (Rf 0.27). Fractions 13-17 from the Sephadex column gave 120 mg. of crude mocimycin, purified on 2 silica gel plates with the same eluant to produce 25 mg. of purified, recovered mocimycin.

The structure of N-demethylefrotomycin was proven by comparison of its $^1$H-NMR and $^{13}$C-NMR spectra with those of efrotomycin. Thus efrotomycin alone shows a singlet due to the three N-methyl hydrogens at 3.4 ppm and a peak at 35 ppm due to the carbon of the N-methyl group. These signals are absent from the spectra of N-demethylefrotomycin. Otherwise, the spectra are virtually identical.

We claim:
1. N-Demethylefrotomycin.
2. A method of treating an infection in a domestic animal due to susceptible bacteria which comprises administering to said animal the compound of claim 1 in an antibacterially effective amount.

* * * * *